(12) United States Patent
Reddy et al.

(10) Patent No.: US 10,945,471 B1
(45) Date of Patent: Mar. 16, 2021

(54) GARMENT

(71) Applicants: Adisesha B. Reddy, Tuscaloosa, AL (US); Juan Carrasquilla, Slidell, LA (US)

(72) Inventors: Adisesha B. Reddy, Tuscaloosa, AL (US); Juan Carrasquilla, Slidell, LA (US)

( * ) Notice: Subject to any disclaimer, the term of this patent is extended or adjusted under 35 U.S.C. 154(b) by 164 days.

(21) Appl. No.: 16/414,993

(22) Filed: May 17, 2019

(51) Int. Cl.
| A41D 13/12 | (2006.01) |
| A41B 9/02 | (2006.01) |
| A61F 13/496 | (2006.01) |
| A61F 13/84 | (2006.01) |

(52) U.S. Cl.
CPC .......... *A41D 13/1254* (2013.01); *A41B 9/026* (2013.01); *A61F 13/496* (2013.01); *A41B 2300/22* (2013.01); *A41B 2300/32* (2013.01); *A41B 2300/328* (2013.01); *A41B 2400/36* (2013.01); *A41B 2400/60* (2013.01); *A61F 2013/8408* (2013.01)

(58) Field of Classification Search
CPC .... A41D 13/1254; A41D 13/12; A41B 9/026; A41B 2300/328
See application file for complete search history.

(56) References Cited

U.S. PATENT DOCUMENTS

| 4,446,575 A | * | 5/1984 | Davis | A41D 13/1254 2/400 |
| 4,930,161 A | * | 6/1990 | Cohen | A41D 13/1254 2/114 |
| 4,932,161 A | * | 6/1990 | Keys | B60J 10/24 49/374 |
| 5,669,902 A | * | 9/1997 | Sivilich | A61F 5/4401 604/385.14 |
| 6,102,899 A | * | 8/2000 | Yimin | A61F 13/84 604/385.01 |
| 8,087,098 B2 | * | 1/2012 | Kimberly | A41B 9/001 2/400 |
| 10,172,747 B2 | * | 1/2019 | May | A61F 13/4915 |
| 2006/0206085 A1 | * | 9/2006 | Gegelys | A61F 13/471 604/385.14 |

* cited by examiner

*Primary Examiner* — Tajash D Patel
(74) *Attorney, Agent, or Firm* — Edward P Dutkiewicz

(57) ABSTRACT

A garment comprising a right leg passageway and a left leg passageway and a trunk portion. The trunk portion has an opening with an edge there through with an associated flap which overlaps the edge of the trunk portion. The trunk portion has at least one coupling strip placed adjacent the edge of the trunk portion opening. The flap has a coupling strip and an absorbent area having an absorbent material being fixedly attached to the absorbent area.

15 Claims, 6 Drawing Sheets

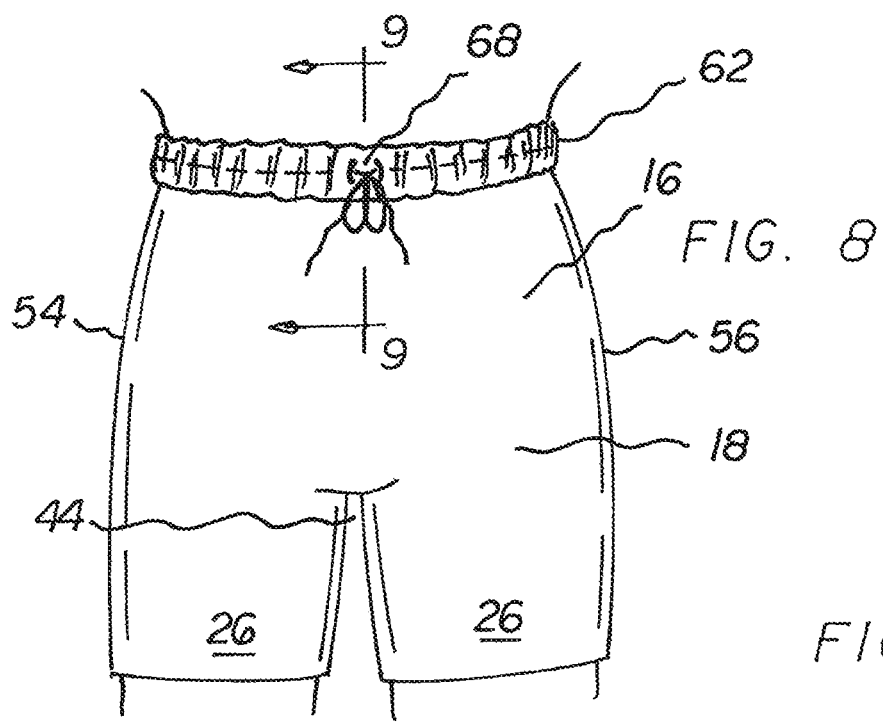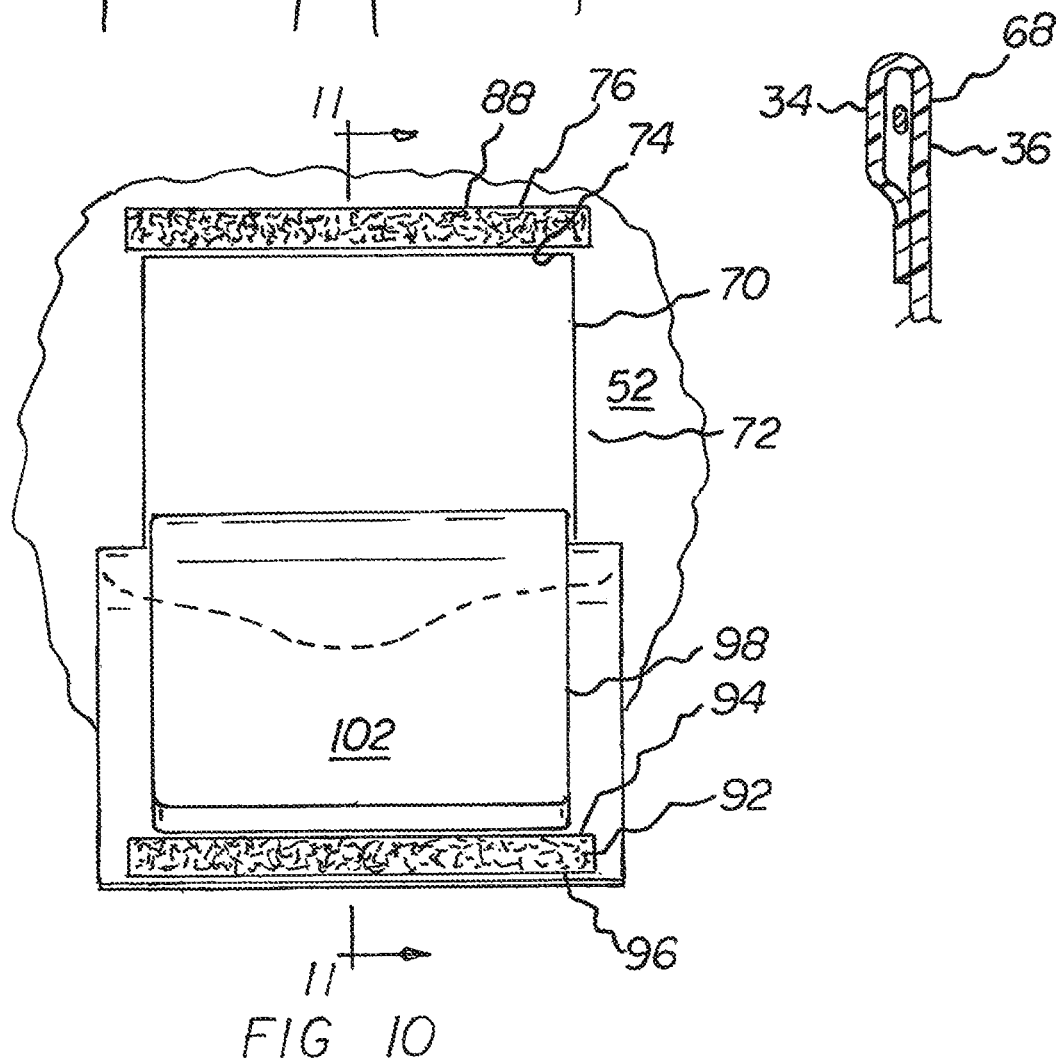

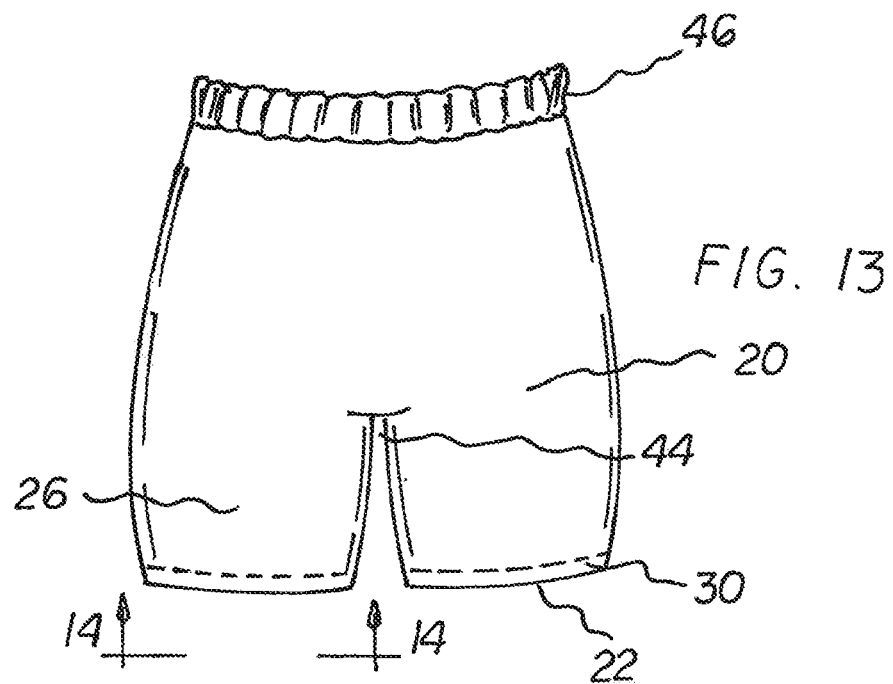
FIG. 13
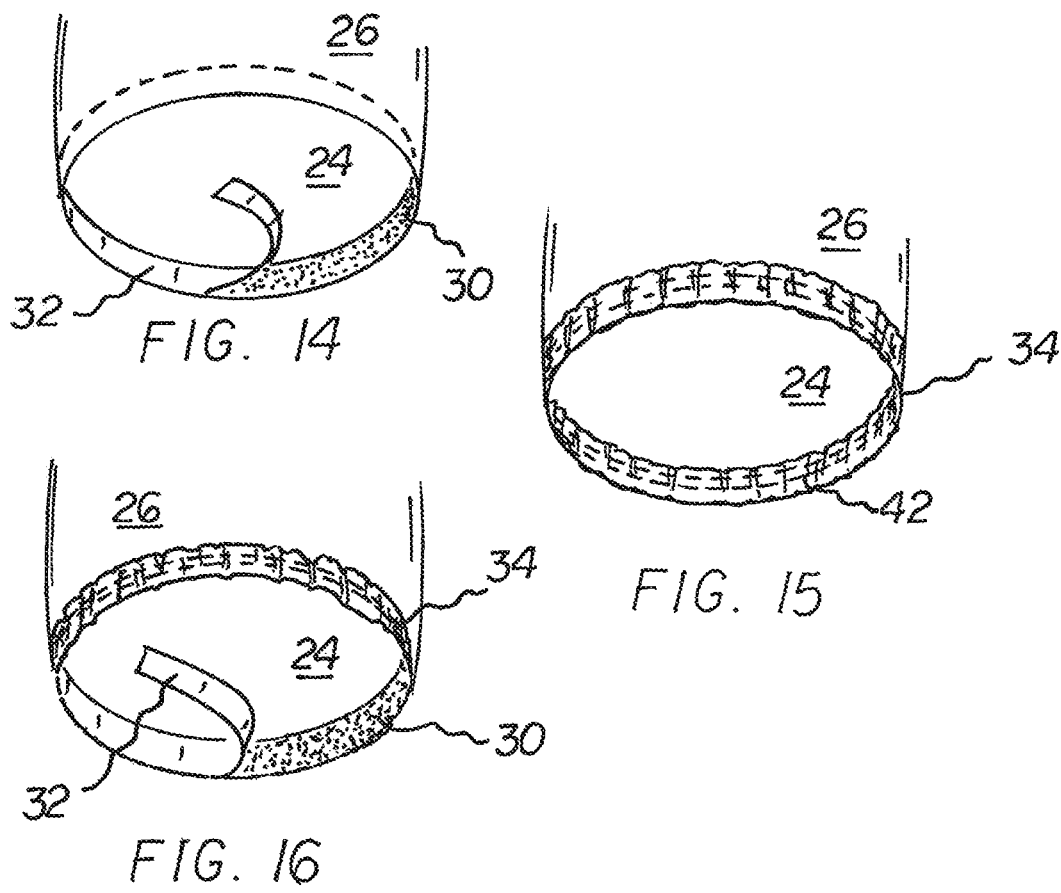
FIG. 14
FIG. 15
FIG. 16

GARMENT

BACKGROUND OF THE INVENTION

Rule 1.78(F)(1) Disclosure

The Applicants have not submitted a related pending or patented non-provisional application within two months of the filing date of this present application. All inventors are herein disclosed. This application is not under assignment to any other person or entity at this time.

FIELD OF THE INVENTION

The present invention relates to a garment and more particularly pertains to garment for use during diagnostic procedures.

DESCRIPTION OF THE PRIOR ART

The use of garments to clothe patients during diagnostic procedures is known in the prior art. More specifically, garments to clothe patients during diagnostic procedures previously devised and utilized for the purpose of providing garments for users are known to consist basically of familiar, expected, and obvious structural configurations, notwithstanding the number of designs encompassed by the prior art which has been developed for the fulfillment of countless objectives and requirements.

While the prior art devices fulfill their respective, particular objectives and requirements, the prior art does not describe a garment that clothes a user and provides diagnostic access.

In this respect, the garment, according to the present invention, substantially departs from the conventional concepts and designs of the prior art, and in doing so provides an apparatus primarily developed for the purpose of providing a garment for use during diagnostic procedures.

Therefore, it can be appreciated that there exists a continuing need for a new and improved garment which can be used during diagnostic procedures. In this regard, the present invention substantially fulfills this need.

SUMMARY OF THE INVENTION

In view of the foregoing disadvantages inherent in the known types of garments to clothe patients during diagnostic procedures now present in the prior art, the present invention provides an improved garment. As such, the general purpose of the present invention, which will be described subsequently in greater detail, is to provide a new and improved garment and method which has all the advantages of the prior art and none of the disadvantages.

In describing this invention, the word "coupled" is used. By "coupled" is meant that the article or structure referred to is joined, either directly, or indirectly, to another article or structure. By "indirectly joined" is meant that there may be an intervening article or structure imposed between the two articles which are "coupled". "Directly joined" means that the two articles or structures are in contact with one another or are essentially continuous with one another.

By adjacent to a structure is meant that the location is near the identified structure.

To attain this, the present invention essentially comprises a garment comprising several components, in combination. There is a right leg passageway and a left leg passageway and a trunk portion. The right leg passageway and the left leg passageway each comprise a generally circumferential wall having an upper extent, a lower extent, an inner surface, and an outer surface. The lower extent of the right leg passageway and the lower extent of the left leg passageway each have a generally circumferential opening. The right leg passageway lower extent inner surface and the left leg passageway lower extent inner surface each have an adhesive layer with a cover removably coupled there to, which allows the lower extent of the right leg passageway and the lower extent of the left leg passageway to become adherent to a user's leg.

In a variation of the preferred embodiment, the right leg passageway lower extent and the left leg passageway lower extent have a stretchable band having a folded portion forming a passageway therein. The stretchable band folded portion passageway has a coupling area and a reflected area. The stretchable band folded portion passageway has at least one elastomeric member contained within the stretchable band folded portion, thereby allowing for the stretching and contracting of the stretchable band around a user's leg.

The stretchable band has an inner surface, with the inner surface of the stretchable band having the adhesive layer. The adhesive layer of the stretchable band has a cover which is removably coupled there to. This allows a user to pull the garment into position before pulling off the cover of the adhesive layer, and coupling the lower extent of the right leg passageway lower extent and the left leg passageway lower extent to the user's right leg and left leg respectively.

The right leg passageway upper extent and the left leg passageway upper extent each are each continuous with the upper trunk portion, thereby forming a crotch there between. The upper trunk portion has a superior extent and a inferior extent. The inferior extent of the trunk is continuous with both the upper extent of the right leg passageway and the upper extent of the left leg passageway. The trunk portion has a front surface, a rear surface, a right side surface, a left side surface, an inner surface, and an outer surface. The front surface of the trunk portion, the rear surface of the trunk portion, the right side surface of the trunk portion, and the left side surface of the trunk portion being continuous.

The trunk portion superior extent has a waist band. The waist band has a folded portion which forms a passageway therein. The waist band folded portion passageway has a coupling area and a reflected area. The waist band folded portion passageway has at least one elastomeric member contained within the folded portion passageway, thereby allowing for the stretching and contracting of the waist band.

The trunk portion rear surface has a opening there through. The trunk portion rear surface opening has an edge which defines the extent of the trunk portion rear surface opening. The trunk portion rear surface opening edge has an inner extent and an outer extent, which defines an area between the inner extent and the outer extent. The trunk portion rear surface opening edge has an inner surface and an outer surface.

The trunk portion rear surface opening has an associated flap. The trunk portion rear surface opening flap has an opening overlapping edge which overlaps the edge of the trunk portion rear surface opening. The flap overlapping edge is positioned to contact the trunk portion rear surface opening edge area.

The trunk portion having at least one coupling strip placed on the edge area of the trunk portion rear surface opening edge. The coupling strip has an inner extent. A coupling strip may be any one of the class of coupling strips that includes hook and loop strips, adhesive strips, snaps, and clips.

The flap overlapping edge has a coupling strip with an inner extent and an outer extent. The inner extent of the flap overlapping edge coupling strip defines an absorbent area and the absorbent area extent. The absorbent area has at least one layer of an absorbent material. The absorbent material is fixedly attached to the absorbent area.

The flap has an open orientation and a closed orientation. The closed orientation has the coupling strip of the flap and the coupling strip of the trunk portion rear surface opening edge being engaged, thereby holding the flap overlapping edge against the edge of the trunk portion rear surface opening edge.

The trunk rear surface inner surface has an adhesive strip coupled thereto. The adhesive strip of the trunk rear surface inner surface has a removable covering layer. The trunk inner surface adhesive strip is positioned substantially around the rear surface opening edge inner surface.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved garment which has all of the advantages of the prior art garments to clothe patients during diagnostic procedures and none of the disadvantages.

It is another object of the present invention to provide a new and improved garment which may be easily and efficiently manufactured and marketed.

It is further object of the present invention to provide a new and improved garment which is of durable and reliable constructions.

An even further object of the present invention is to provide a new and improved garment which is susceptible of a low cost of manufacture with regard to both materials and labor, and which accordingly is then susceptible of low prices of sale to the consuming public, thereby making such garment economically available to the buying public.

Even still another object of the present invention is to provide a garment for use during diagnostic procedures.

Lastly, it is an object of the present invention to provide a new and improved garment comprising a right leg passageway and a left leg passageway and a trunk portion. The trunk portion has an opening with an edge there through with an associated flap which overlaps the edge of the trunk portion. The trunk portion has at least one coupling strip placed adjacent the edge of the trunk portion opening. The flap has a coupling strip and an absorbent area having an absorbent material being fixedly attached to the absorbent area.

It should be understood that while the above-stated objects are goals which are sought to be achieved, such objects should not be construed as limiting or diminishing the scope of the claims herein made.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 8 is a front elevational view, showing the tie being used rather than an elastomeric band within the waist band.

FIG. 9 is a view taken along line 9-9 of FIG. 8.

FIG. 10 is a close up view of the flap showing a flap which is rotatable in a downward direction.

FIG. 13 is a front elevational view of the garment having an adhesive strip along the lower extent of each leg.

FIG. 14 is a view taken along line 14-14 of FIG. 13.

FIG. 15 is a bottom perspective close up view of the lowermost extent of a leg showing the lowermost extent having an elastomeric band around the extent.

FIG. 16 is a bottom perspective close up view of the lowermost extent of a leg showing the lowermost extent having an elastomeric band around the extent as well as an adhesive strip within the inner surface of the lowermost extent.

The same reference numerals refer to the same parts throughout the various Figures.

DESCRIPTION OF THE PREFERRED EMBODIMENT

Figure 1:
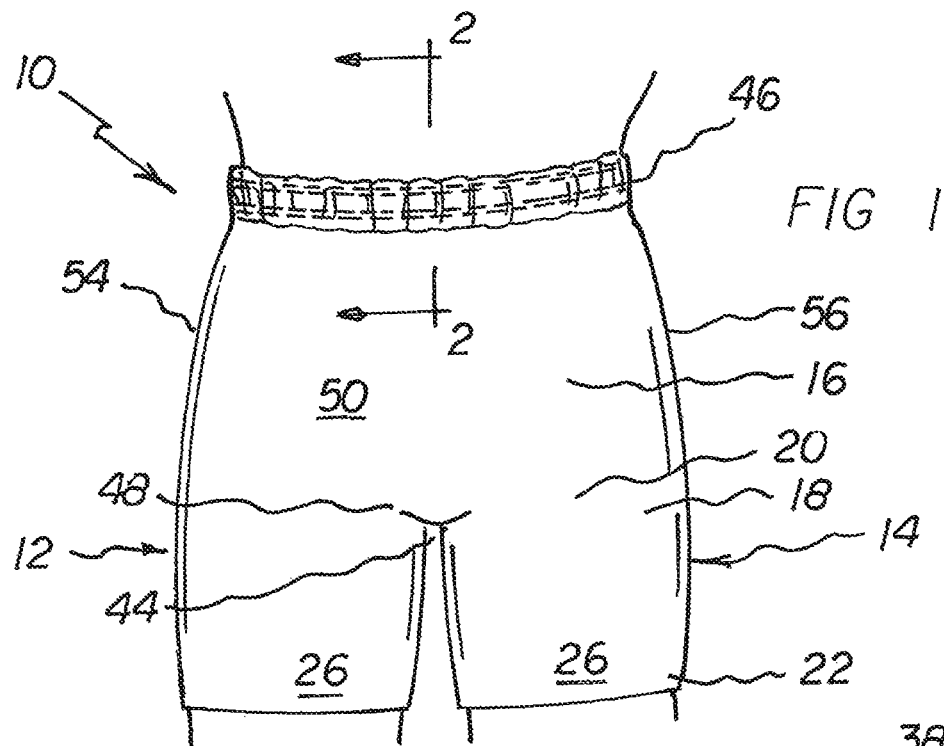
FIG. 1 is a front elevational view of the garment.
Figure 2:
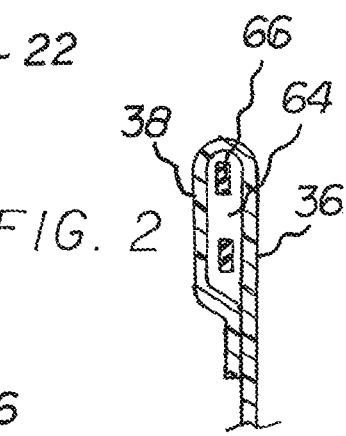
FIG. 2 is a view taken along line 2-2 of FIG. 1.
Figure 3:
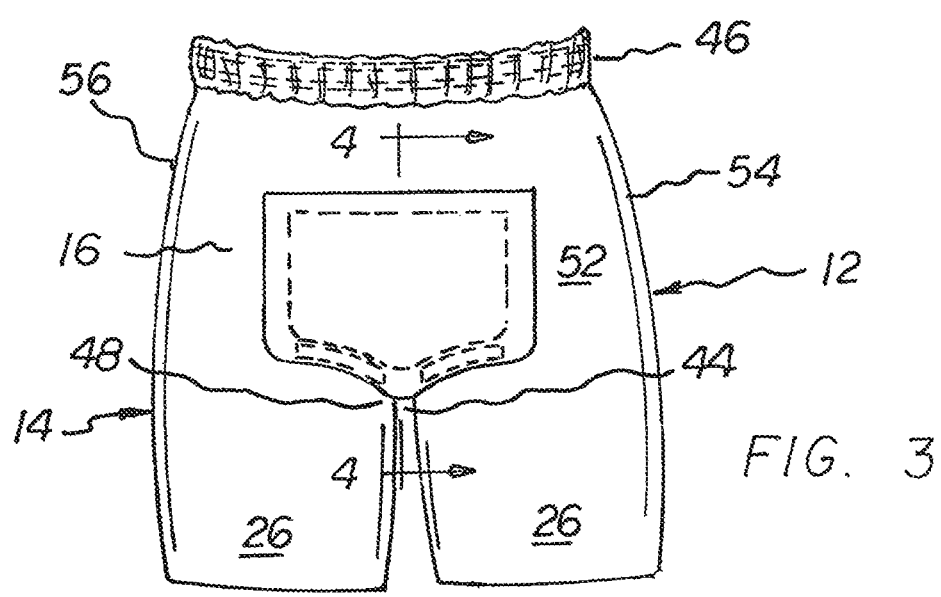
FIG. 3 is a rear elevational view of the garment.
Figure 4:
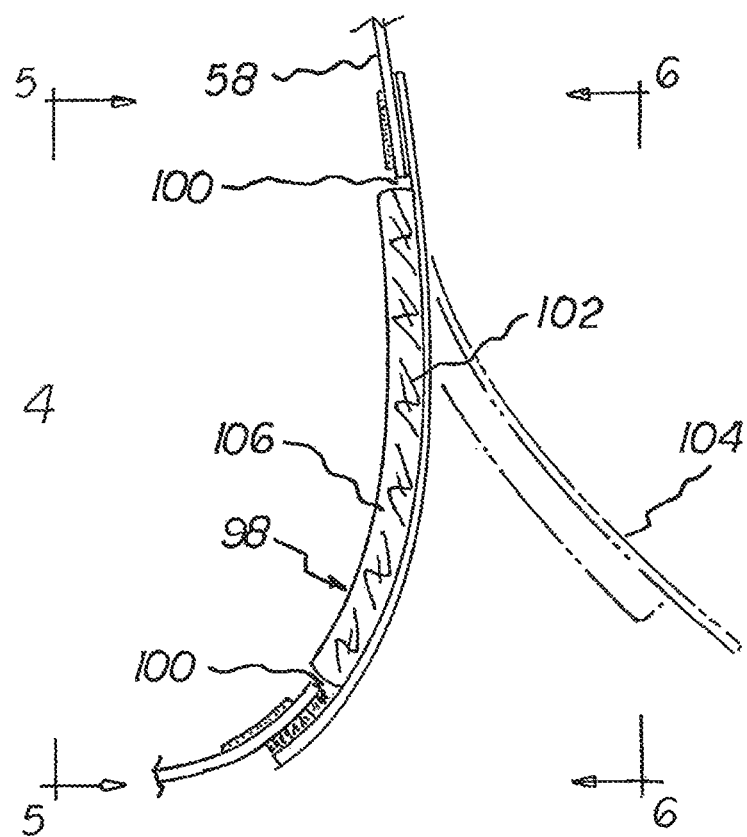
FIG. 4 is a view taken along line 4-4 of FIG. 3.
Figure 5:
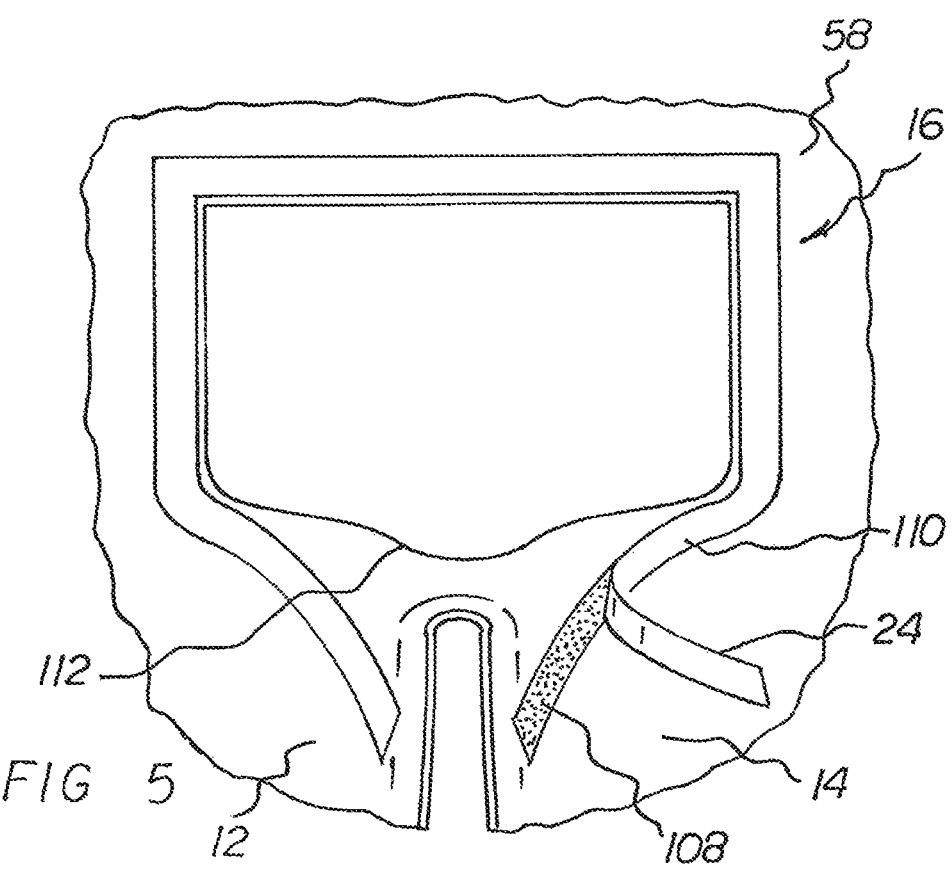
FIG. 5 is a close up view of the rear inner surface of the garment, showing the adhesive strip being located substantially around the opening in the rear surface of the trunk portion of the garment.
Figure 6:
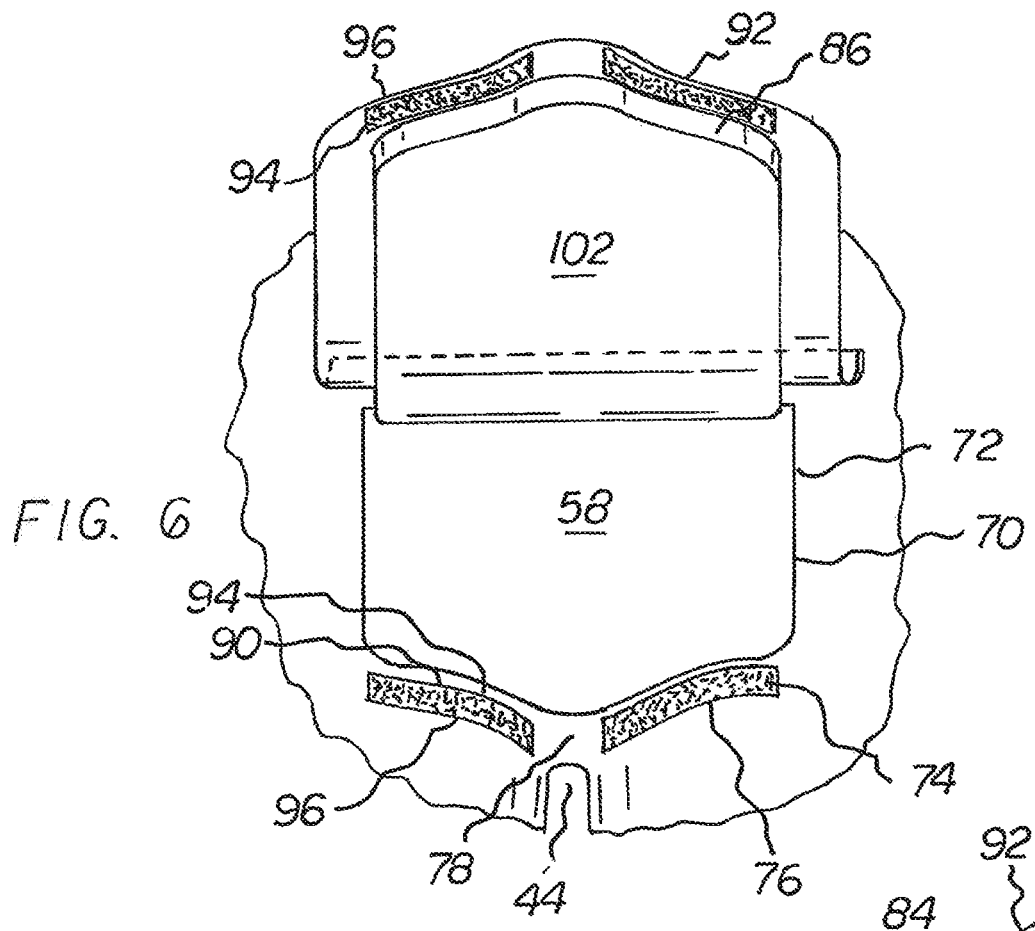
FIG. 6 is a view taken along line 6-6 of FIG. 4.
Figure 7:
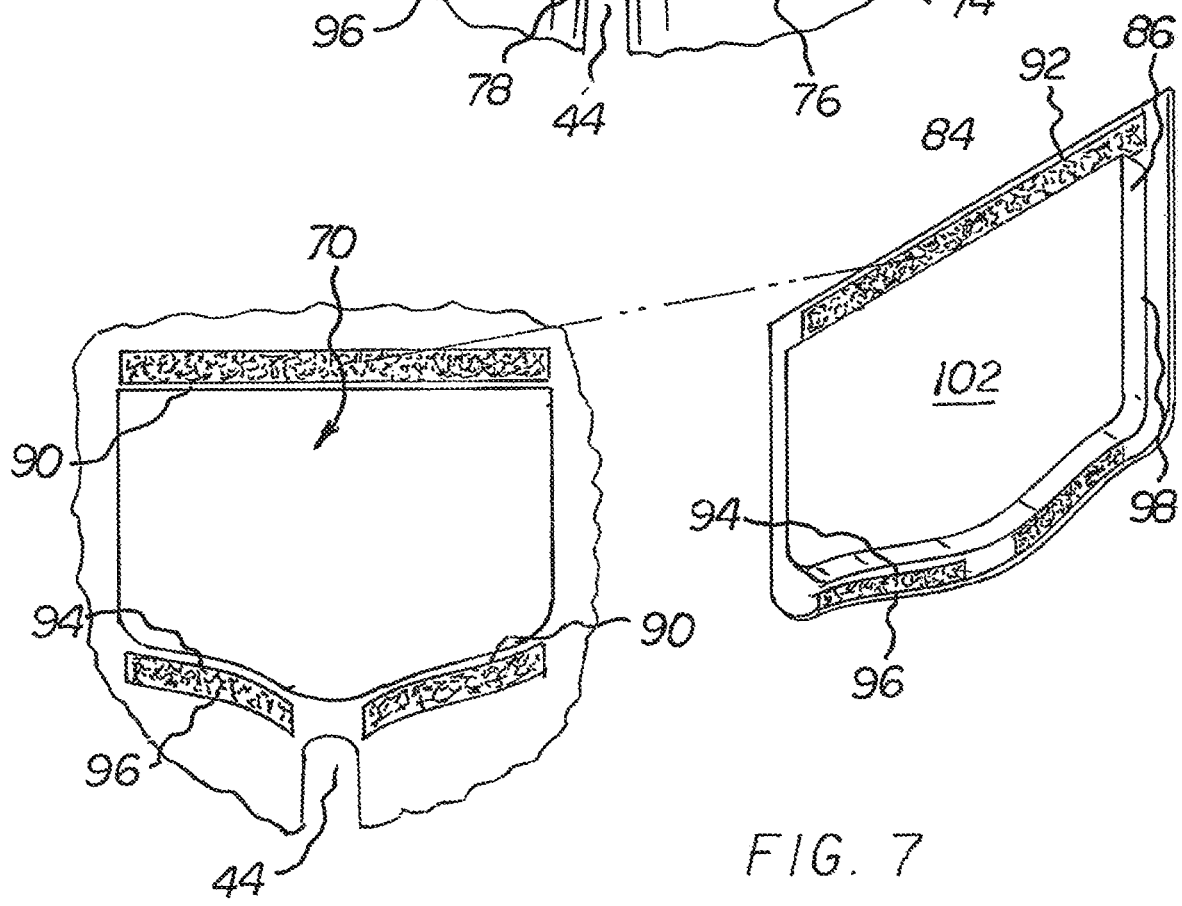
FIG. 7 is a close up view of the trunk rear surface showing the opening with the hook and loop strips for adhering the flap to the opening. The absorbent layer is visible on the removable flap.
Figure 11:
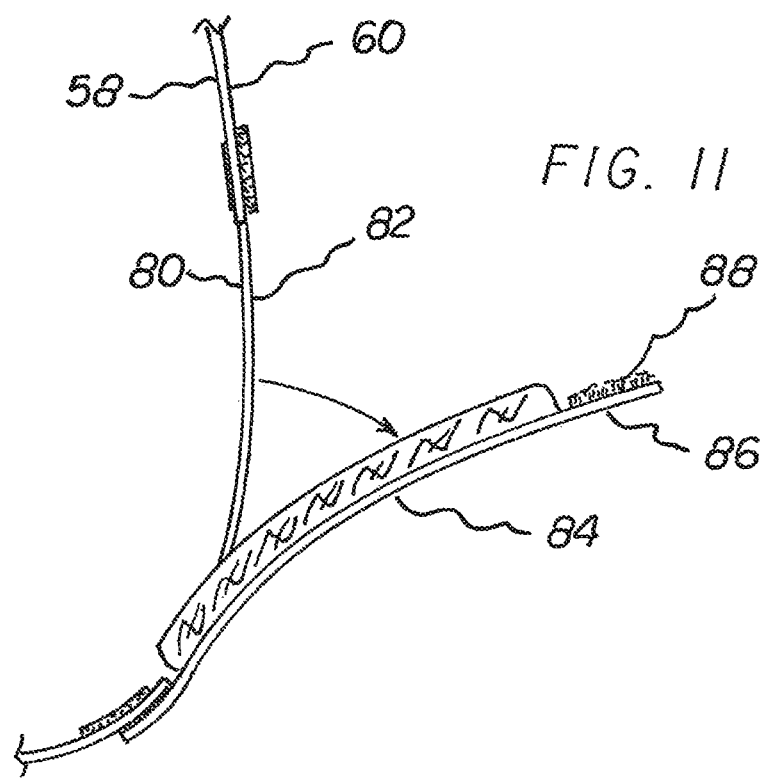
FIG. 11 is a view taken along line 11-11 of FIG. 10.
Figure 12:
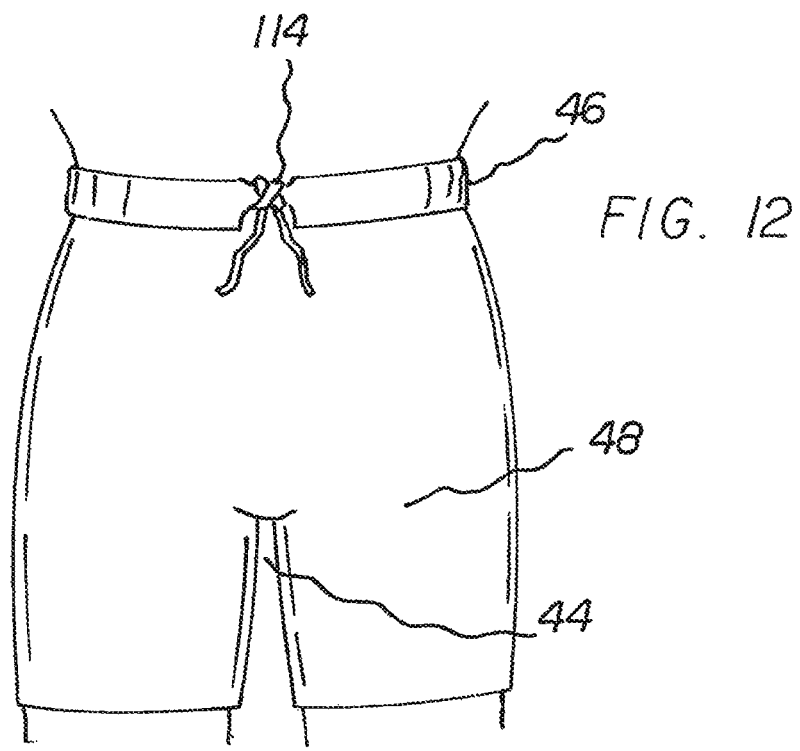
FIG. 12 is a front elevational view of a tie strap being used to secure the garment in position.

With reference now to the drawings, and in particular to FIG. 1 thereof, the preferred embodiment of the new and improved garment embodying the principles and concepts of the present invention and generally designated by the reference numeral 10 will be described.

The present invention, the garment 10 is comprised of a plurality of components. Such components in their broadest context include a trunk portion, a pair of leg portions, a flap and an absorbent coupled to the flap. Such components are individually configured and correlated with respect to each other so as to attain the desired objective.

A garment 10 is herein described. The garment comprises several components, in combination.

There is a right leg passageway 12 and a left leg passageway 14 and a trunk portion 16. The right leg passageway and the left leg passageway each comprise a generally circumferential wall 18 having an upper extent 20, a lower extent 22, an inner surface 24, and an outer surface 26. The lower extent of the right leg passageway and the lower extent of the left leg passageway each have a generally circumferential opening 28.

In a variation of the preferred embodiment, the right leg passageway lower extent inner surface and the left leg passageway lower extent inner surface each have an adhesive layer 30 with a cover 32 removably coupled there to, which allows the lower extent of the right leg passageway and the lower extent of the left leg passageway to become adherent to a user's leg.

In another variation of the preferred embodiment, the right leg passageway lower extent and the left leg passageway lower extent have a stretchable band 34 having a folded portion forming a passageway therein. The stretchable band folded portion passageway has a coupling area 36 and a reflected area 38. The stretchable band folded portion passageway has at least one elastomeric member 40 contained within the stretchable band folded portion, thereby allowing for the stretching and contracting of the stretchable band around a user's leg.

In this variation of the preferred embodiment, the stretchable band has an inner surface 42, with the inner surface of the stretchable band having the adhesive layer 30. The adhesive layer of the stretchable band has the cover 32 which is removably coupled there to. This allows a user to pull the garment into position before pulling off the cover of the adhesive layer, and coupling the lower extent of the right leg passageway lower extent and the left leg passageway lower extent to the user's right leg and left leg respectively.

The right leg passageway upper extent and the left leg passageway upper extent each are each continuous with the upper trunk portion, thereby forming a crotch 44 there between. The upper trunk portion has a superior extent 46 and an inferior extent 48. The inferior extent of the trunk is continuous with both the upper extent of the right leg passageway and the upper extent of the left leg passageway. The trunk portion has a front surface 50, a rear surface 52, a right side surface 54, a left side surface 56, an inner surface 58, and an outer surface 60. The front surface of the trunk portion, the rear surface of the trunk portion, the right side surface of the trunk portion, and the left side surface of the trunk portion are continuous.

The trunk portion superior extent has a waist band 62. The waist band has a folded portion which forms a passageway 64 therein. The waist band folded portion passageway has the coupling area 36 and the reflected area 38. The waist band folded portion passageway has at least one elastomeric member 66 contained within the folded portion passageway, thereby allowing for the stretching and contracting of the waist band.

In another variation of the preferred embodiment, the waist band may, in place of the elastomeric member, have a tie 68 running through the waist band passageway, to allow a user to pull tight the tie, and knot the tie in a comfortable position. The tie configuration would allow a wider range of user sizes to use the garment.

The trunk portion rear surface has a opening 70 there through. The trunk portion rear surface opening has an edge 72 which defines the extent of the trunk portion rear surface opening. The trunk portion rear surface opening edge has an inner extent 74 and an outer extent 76, which defines an area 78 between the inner extent and the outer extent. The trunk portion rear surface opening edge has an inner surface 80 and an outer surface 82.

The trunk portion rear surface opening has an associated flap 84. The trunk portion rear surface opening flap has an opening overlapping edge 86 which overlaps the edge of the trunk portion rear surface opening. The flap overlapping edge is positioned to contact the trunk portion rear surface opening edge area.

The trunk portion having at least one coupling strip 88 placed on the edge area of the trunk portion rear surface opening edge. The coupling strip has an inner extent 90. A coupling strip may be any one of the class of coupling strips that includes hook and loop strips, adhesive strips, snaps, and clips.

The flap overlapping edge has a coupling strip 92 with an inner extent 94 and an outer extent 96. The inner extent of the flap overlapping edge coupling strip defines an absorbent area 98 and the absorbent area extent 100. The absorbent area has at least one layer of an absorbent material 102. The absorbent material is fixedly attached to the absorbent area. The absorbent material may contain a fragrance, or an odor-eliminating chemical so as to provide a pleasant scent or eliminate any unpleasant odor which may be an aspect of any drainage captured by the absorbent material.

The flap has an open orientation 104 and a closed orientation 106. The closed orientation has the coupling strip of the flap and the coupling strip of the trunk portion rear surface opening edge being engaged, thereby holding the flap overlapping edge against the edge of the trunk portion rear surface opening edge.

The trunk rear surface inner surface has an adhesive strip 108 coupled thereto. The adhesive strip of the trunk rear surface inner surface has a removable cover 110. The trunk inner surface adhesive strip is positioned substantially around the rear surface opening edge inner surface 112.

The flap may be either attached to the rear surface of the garment, or it may be removable. In another variation of the preferred embodiment, the waist band may consist of a tie strap 114, which encompasses the waist, and is tied in a comfortable position by the user.

The garment herein described is anticipated to be used in a setting where diagnostic procedures, such as colonoscopy, is performed. This procedure generally requires a user to be disrobed. This garment allows the user to maintain modesty in a compromising situation. In use, the user would disrobe and put on the garment, either tying it in place or allowing the waist band to form the fit around the user's waist. In one embodiment, the user may then remove the cover strip around the leg lower extent openings, and seal the garment around the user's thigh. Once the procedure was about to be initiated, the flap would be either opened or removed, and the adhesive strip around the flap opening would be uncovered, allowing the garment to be adhered to the user's skin. This allows a sealing of the flap area, thereby preventing fluids and material from running down, into the interior of the garment.

At the end of the procedure, the user is cleansed, and the flap returned to the closed orientation. The user can then be transported to a post procedure. The absorbent material on the inner surface of the flap may minimize any leakage or discharge that may occur post diagnostic procedure.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A garment comprising, in combination:

a right leg passageway and a left leg passageway and a trunk portion, the trunk portion having a front surface and a rear surface and a right side surface and a left side surface and an inner surface and an outer surface, with the front surface and a rear surface and a right side surface and a left side surface being continuous, the trunk portion rear surface having an opening there through, with the trunk portion rear surface opening having an edge, with the trunk portion rear surface edge having a terminus and an outermost extent, with the edge terminus defining the innermost extent of the trunk portion rear surface opening, the edge terminus and the edge outermost extent defining an area which surrounds the opening in the trunk portion rear surface, the trunk portion rear surface opening edge having an inner surface and an outer surface, the trunk portion rear surface opening having an associated flap, the trunk portion rear surface opening associated flap having an opening overlapping edge which overlaps the edge of the trunk portion rear surface opening outer surface, the flap overlapping edge being positioned to contact the trunk portion rear surface opening edge area, the trunk portion having at least one coupling strip placed on the edge area of the outer surface of the trunk portion rear surface opening edge with the coupling strip having an inner extent, the flap overlapping edge having a coupling strip with an inner extent and an outer extent, the inner extent of the flap overlapping edge coupling strip defining an absorbent area and an absorbent area extent, the absorbent area having at least one layer of an absorbent material, the absorbent material being fixedly attached to the absorbent area; and the trunk rear surface inner surface having an adhesive strip coupled thereto, with the adhesive strip of the trunk rear surface inner surface having a removable covering layer, the trunk inner surface adhesive strip being positioned substantially around the rear surface opening edge inner surface.

2. The garment described in claim 1, with the garment further comprising:

the right leg passageway and the left leg passageway each comprising a generally circumferential wall having an upper extent and a lower extent and an inner surface and an outer surface, the right leg passageway upper extent and the left leg passageway upper extent each being continuous with the upper trunk portion thereby forming a crotch there between; and the flap having an open orientation and a closed orientation, the closed orientation having the coupling strip of the flap and the coupling strip of the trunk portion rear surface opening edge being engaged thereby holding the flap overlapping edge against the trunk portion rear surface opening edge.

3. The garment described in claim 2, with the garment further comprising the lower extent of the right leg passageway and the lower extent of the left leg passageway each having a generally circumferential opening.

4. The garment described in claim 3, with the garment further comprising:

the right leg passageway lower extent inner surface and the left leg passageway lower extent inner surface each having an adhesive layer with a cover removably coupled there to, which allows the lower extent of the right leg passageway and the lower extent of the left leg passageway to adherent to a user's leg; and the adsorbent material comprising a fragrance.

5. The garment described in claim 4, with the garment further comprising the upper trunk portion having a superior extent and a inferior extent, with the inferior extent of the trunk being continuous with the upper extent of the right leg passageway and the upper extent of the left leg passageway.

6. The garment described in claim 5, with the garment further comprising the trunk portion superior extent having a waist band.

7. The garment described in claim 6, with the garment further comprising:

the right leg passageway lower extent and the left leg passageway lower extent having a stretchable band having a folded portion forming a passageway therein, the stretchable band folded portion passageway having a coupling area and a reflected area; and the waist band having a folded portion forming a passageway therein, the waist band folded portion passageway having a coupling area and a reflected area.

8. The garment described in claim 7, with the garment further comprising:

the right leg passageway lower extent and the left leg passageway lower extent stretchable band folded portion passageway having at least one elastomeric member contained within the stretchable band folded portion thereby allowing for the stretching and contracting of the stretchable band around a user's leg; and the waist band folded portion passageway having at least one elastomeric member contained within the folded portion passageway thereby allowing for the stretching and contracting of the waist band.

9. The garment described in claim 8, with the garment further comprising the right leg passageway lower extent and the left leg passageway lower extent stretchable band having an inner surface, with the inner surface of the stretchable band having the adhesive layer with the cover removably coupled there to.

10. A garment, comprising, in combination:

a right leg passageway and a left leg passageway and a trunk portion, the trunk portion having a front surface and a rear surface and an inner surface and an outer surface, the trunk portion rear surface having an opening there through, the opening in the trunk portion rear surface having an edge and an edge area, with the trunk portion rear surface opening having an associated flap, the trunk portion rear surface opening associated flap overlaps the edge of the trunk portion rear surface opening outer surface, the trunk portion having at least one coupling strip placed on the edge area of the outer surface of the trunk portion rear surface opening edge, the flap overlapping edge having a coupling strip, the flap overlapping edge coupling strip defining an absorbent area and an absorbent area extent, the absorbent area having at least one layer of an absorbent material, the absorbent material being fixedly attached to the absorbent area; and the trunk rear surface inner surface having an adhesive strip coupled thereto, with the adhesive strip of the trunk rear surface inner surface having a removable covering layer, the trunk inner surface adhesive strip being positioned substantially around the rear surface opening edge inner surface.

11. The garment described in claim 10, with the garment further comprising the trunk portion having a superior extent with the superior extent of the trunk portion having a waist band, the waist band having a folded portion forming a passageway therein, the waist band folded portion passageway having a coupling area and a reflected area.

12. The garment described in claim 11, with the garment further comprising the waist band folded portion passageway having at least one elastomeric member contained within the folded portion passageway thereby allowing for the stretching and contracting of the waist band.

13. The garment described in claim 12, with the garment further comprising the right leg passageway having a lower extent and the left leg passageway having a lower extent, with the right leg passageway lower extent and the left leg passageway lower extent each having a stretchable band with the stretchable band of each leg passageway having a folded portion forming a passageway therein, each leg passageway stretchable band folded portion passageway having a coupling area and a reflected area, each stretchable band folded portion passageway having at least one elastomeric member contained within the stretchable band folded portion thereby allowing for the stretching and contracting of the stretchable band around a user's leg.

14. The garment described in claim 13, with the garment further comprising the right leg passageway lower extent stretchable band and the left leg passageway lower extent stretchable band having an inner surface, with the inner surface of the stretchable band having the adhesive layer with the cover removably coupled there to.

15. The garment described in claim 1, with the garment further comprising the adsorbent material comprising an odor eliminating chemical so as to eliminate unpleasant odor.

* * * * *